United States Patent [19]

Golwyn

[11] Patent Number: 4,919,916
[45] Date of Patent: * Apr. 24, 1990

[54] TREATMENT OF NEUROTRANSMITTER-LINKED DRUG ABUSE

[76] Inventor: Daniel H. Golwyn, 701 E. Semoran Blvd., Altamonte Springs, Fla. 32715

[*] Notice: The portion of the term of this patent subsequent to Nov. 22, 2005 has been disclaimed.

[21] Appl. No.: 273,777

[22] Filed: Nov. 21, 1988

Related U.S. Application Data

[63] Continuation-in-part of Ser. No. 88,830, Aug. 24, 1987, Pat. No. 4,786,653.

[51] Int. Cl.$^5$ .............................................. A61K 27/00
[52] U.S. Cl. .................................... 424/10; 514/810; 514/812
[58] Field of Search .................... 424/10; 514/810, 812

[56] References Cited
U.S. PATENT DOCUMENTS
3,000,903  9/1961  Biel ...................................... 549/440

Primary Examiner—Stanley J. Friedman
Attorney, Agent, or Firm—Charles A. McClure

[57] ABSTRACT

Treatment of the abuse of those addictive drugs whose apparent mode of operation includes first an enhancement of neurotransmitter activity and subsequently a reduction in that activity—and in accompanying pleasurable sensations—to such an extent that abusers thereof feel compelled to repeat the experience. Examples of abused drugs for which treatment is suitable are amphetamines, cocaine, meperidine, phencyclidine, and new "designer" drugs. The treatment is by daily dosage of phenelzine or equivalent phenylalkylhydrazine so as to effect a degree of monoamine oxidase inhibition incompatible with the abused drug during the period of treatment and for at least a couple weeks thereafter. Concurrent usage is productive of a broad range of dangerous and frightening reactions, described in graphic detail to all patients undergoing such treatment, and any breach of the prohibition confirms the necessity of remaining free of the abused drug throughout. The treatment is effective in producing at least temporary and frequently longer-lasting abstinence.

5 Claims, No Drawings

TREATMENT OF NEUROTRANSMITTER-LINKED DRUG ABUSE

This is a continuation-in-part of my similarly titled copending patent application, Ser. No. 88,830 filed 24 Aug. 1987 now U.S. Pat. No. 4,786,653 granted 22 Nov. 1988.

TECHNICAL FIELD

This invention relates to therapeutic treatment of the abuse of drugs that are effective in enhancing neurotransmitter activity temporarily and in subsequently depressing such activity—such as amphetamines, cocaine, and others similarly addictive.

BACKGROUND OF THE INVENTION

It is common knowledge that humans, as well as lower animals, become euphoric or otherwise "high" from taking certain drugs, to some of which they may be introduced for medical reasons but many of which are available for non-medical use—usually deemed abuse. Effects of such drugs include enhancing concentration or activity of neurotransmitters (e.g., dopamine, norepinephrine, epinephrine, serotonin), which is an immediate inducement to use of such a drug by those who abuse it; and such effects also include subsequently depressing such neurotransmitter characteristics—an inducement to one more use, at least for many users, who thereupon undertake to abuse such drug repeatedly, to bodily and financial limits.

Though many, presumably most, persons do not take such drugs except as prescribed by physicians, numerous other persons become so addicted to using such drugs that they engage in a wide variety of anti-social acts to buy or otherwise obtain them—via a network of illegal production and delivery activities, means, and methods. Attempted interdiction of drugs subject to such excessive demand raises the cost to users and the profits to suppliers, and tends to corrupt otherwise law-abiding persons by inducing bribery, etc.

Attempts to treat users of such drugs, as by administering a less harmful drug in place thereof, have met with limited success because users tend to prefer immediate though transitory pleasure received from abused drugs to pleasure-lessening drug treatments. Substitution of another pleasurable drug, intended to be withdrawn more readily than an abused drug, also tends to fail, for an addict may merely take such substitute drug until the treatment ends, and then return to the abused drug as soon as possible thereafter.

A very substantial need exists for a therapeutic treatment of neurotransmitter-linked drug abuse that not only will wean abusers of such drugs away from their abused drugs but also will keep such abusers from returning to such abused drugs when the treatment has ended. This patent specification of mine discloses such treatment.

SUMMARY OF THE INVENTION

A primary object of the present invention is to treat abusers of neurotransmitter-linked drugs with a pharmaceutical effective to discontinue such drug use by such abusers.

Another object of this invention is to provide such treatment as to render such a drug abuser physically incapable of tolerating concurrent use of the abused drug.

A further object of the invention is to provide such treatment as to render such a drug abuser physically and mentally unlikely to use such abused drug after termination of such treatment.

Another object is to provide compositions with an acceptable pharmaceutical carrier, especially for such use in such treatment.

A still further object is to package such compositions with markings indicating such intended use and with directions therefor.

In general, the objects of this invention are accomplished by administering to a person who uses a neurotransmitter-linked drug unnecessarily a phenylalkylhydrazine so as to effect at least a temporary and preferably a permanent discontinuation of such use.

Other objects of this invention, together with methods and means for accomplishing the various objects, will be apparent from the following description, presented here by way of example rather than limitation.

DETAILED DESCRIPTION OF THE INVENTION

Active ingredients suitable for use according to my invention are disclosed—but without any mention whatever of such use—in Biel U.S. Pat. No. 3,000,903 (Lakeside Laboratories, Inc.) entitled "Phenylalkylhydrazines, and Use as Psychotherapeutics"—but whose use according to my invention is not disclosed there or elsewhere.

The Biel patent describes numerous phenylalkylhydrazines, their preparation, and uses. Their principal suggested use is as psychotherapeutics, specifically as inhibitors of the natural metabolic conversion or destruction of neurotransmitters in the brain by monoamine oxidase (MAO). Such inhibitory activity, or MAOI, is considered to be anti-depressant, inasmuch as depletion of neurotransmitters may interfere with a customary sense of well being sufficiently to give rise to a feeling of depression. MAOI is conducive to assertiveness, motivation, and self-confidence and to reducing anxiety, indecisiveness, perfectionism, and phobias.

Biel notes especially as "most potent" the MAOI activity of phenylalkylhydrazines with up to three carbon atoms in the straight portion of the hydrocarbon chain between the phenyl group and the substituted hydrazine residue, viz., the phenylethyl, phenylpropyl, and phenylbutyl hydrazines, including those with branched (iso-) or normal (n-) chains, and also those with possible substituents, such as lower alkyl, lower alkoxy, or halogen in the phenyl group.

Biel indicates clinical improvement from administration of a specifically chosen phenylalkylhydrazine as evidenced by alertness, elevation of mood, and diminution of confusion, and by reduction in depressive attitudes. He singles out phenylisopropylhydrazine or, more technically, N-(3-phenyl-2-propyl)-hydrazine as an example.

Also singled out by Biel for special recommendation are a half dozen additional single-N-substituted phenylalkylhydrazines: (3-p-methoxyphenyl-2-propyl)-hydrazine, (3-o-methylphenyl-2-propyl)-hydrazine, [3(3',4'-methylenedioxy)-phenyl-2-propyl]-hydrazine, (2-phenyl-1-propyl)-hydrazine, (4-phenyl-2-butyl)-hydrazine, and (3-m-chlorophenyl-2-propyl)-hydrazine. Example 5 of the patent is drawn to production of phenylisopropylhydrazine; whereas Example 6 is drawn to its hydrochloride salt. Examples 1 and 2 are similarly devoted to phenelzine (2-phenethyl)hydrazine and its similar salt.

The psychotherapeutic pharmaceuticals of the Biel patent are prime candidates for use in treating drug abusers according to this invention. The one last mentioned, phenelzine (Merck Index 7089), is the therapeutic phenylalkylhydrazine of choice for use according to the present invention and is readily available (with a carrier) under the brand name "Nardil" (Parke-Davis). Also suitable to be so considered, as well as others meeting Biel's structural preference are mebanazine or (1-phenylethyl)hydrazine (M.I. 5588) and pheniprazine or (1-methyl-2-phenethyl)-hydrazine (M.I. 7105).

Whichever of the aforementioned pharmaceuticals is selected, however, it is administered in a pharamaceutically acceptable carrier, such as suggested in the aforementioned Biel patent or as otherwise would be readily selected by persons ordinarily skilled in the phrmaceutical art. Moreover, it is used as follows in such treatment, subject to whatever variation may be deemed best by the physician in charge.

First, patients are diagnosed as abusers of drugs that appear to be linked to neurotransmitters by an enhancement effect thereon and, therefore, likely to be susceptible to aid by this treatment. It is understandable that diverse drugs may have various significant modes of influence and still be amenable to treatment according to this invention, so the suggested theory of operation is intended as a guide rather than as a limitation or a sine qua non for treatment. Notable candidates for such treatment are abusers of amphetamines, cocaine, meperidine, phencyclidine (PCP), or new "designer" drugs.

Detailed drug histories having been taken, the patients are screened to confirm presence of factors conducive to successful treatment (or to exclude as patients those with serious negative factors) unless other considerations permit or require a broader study.

Motivation, intelligence, and dependability of patients should be ascertained in view of the importance of the patients' taking of the prescribed medication regularly for success of the treatment and of the risk of ingesting such abused drugs while undergoing treatment with an intentional MAO inhibitor.

MAOI dietary restrictions are explained and must be followed to avoid unnecessary complications, such as hypertensive reaction. For example, foods high in tyramine (which is structurally related to norepinephrine) should be avoided, such as aged cheese, pickled herring, and poorly preserved meats. Chinese snow peas, Italian fava beans, and yeast tablets, are further examples to be avoided. Persons with prior liver damage or related defect are preferably disqualified from being treated. Such instructions are given to the patient in writing as well as orally, preferably printed on the medication package along with a warning against taking any of the drugs (listed) whose discontinuation is the goal of the treatment. An especial effort is made to establish a feeling of mutual trust with each patient in view of the strong affective nature of drug addiction and treatment.

The chosen pharmaceutical, e.g., phenelzine, in such carrier is administered to qualified patients, preferably orally, every day or substantially so, and preferably several times each day. It is conveniently administered in dosage units of 15 milligrams, a standard recommended dose thereof for use as an antidepressant. Three times that amount daily, or a total of 45 milligrams proves adequate for some patients, but for others it is increased stepwise (such as to 60, 75, or 90 mg). A preferred dosage reduces blood pressure when the patient goes from a sitting to standing position and from standing to jogging in place—with adequate blood pressure throughout. Daily dosage is limited to at most about a hundred mg.

Notable side effects or potential disadvantages of treatment according to this invention are dizziness and fainting, both of which are avoidable by proper dosage. Frequent checking of blood pressure not only is helpful in avoiding undue hypotension but also confirms actual taking of the medication by the patient(s). Any patients with habitually low blood pressure are urged to drink more coffee or tea and to increase their intake of other fluids and salt. Treatment according to this invention may continue for as short a period as several to a half dozen weeks to as long as a half dozen to a dozen months. The total time is difficult to predict because of the inestimable contribution made by the patient's own will.

So long as a patient is under such treatment, concurrent use of an abused drug is not very likely because of the substantial likelihood of adverse effects—of which the patient has been well informed in advance of treatment both orally and in writing, such as on the medication package or instructions contained therein. The drastic nature of such effects underscores the desirability of ensuring cooperation on the part of everyone accepted for treatment. Potential very unpleasurable effects include headaches, delirium, severe shock, blood pressure increases, palpitations, and heart heart failure possible culminating in death, even with as common a substance as meperidine—a brand name being "Demerol" (Winthrop).

Patient resistance to the treatment is lessened by the fact that administered phenylalkylhydrazine increases neurotransmitter concentration somewhat but without subsequent drastic reduction customarily associated with coming down from an abused drug high, for example. Moreover, as a patient becomes stabilized mentally and physically, dosage is reduced to the initial level or lower, so that termination of the treatment does not evoke withdrawal symptoms, and the patient need not resume using cocaine, etc. A program of surprise urine sampling and testing is recommended.

It is noteworthy that other therapeutic treatments suggested for the same purpose as the treatment of the present invention do not attain such results. For example, treatment with imipramine or desipramine does not block concurrent use (or high) of cocaine and may encourage its use by blocking the depression induced by cocaine, etc. from such treatment; also, bromocriptine, which otherwise might appear suitable, is productive of panic, hallucinations, and related fright reactions so that patients cannot always be relied upon to continue taking it. Other previously suggested treatments have their own disadvantages.

Phenelzine or other phenylalkylhydrazine of this invention, on the other hand, is just pleasurable enough that patients do not want to discontinue it for a period of about two weeks after this treatment, as is necessary before they can tolerate cocaine again. Faced with such a choice, many patients can choose and stick with phenelzine or other suitable pharmaceutical according to this invention—avoiding cocaine, etc.—and eventually abandon both.

Advantages of the present invention are mentioned above and are generally obvious, but other advantages doubtless will become apparent to qualified persons who undertake to treat drug abusers according to this invention, as well as to persons so treated.

Acceptable ranges and variations in compositions, dosages, times, etc. have been mentioned also, and other changes may be made, as in procedures and steps, instructions and packaging, while retaining at least some of the benefits of the present invention—which itself is defined in the following claims.

I claim:

1. A method of treating abusers of a drug likely to enhance neurotransmitter activity in the short term and to depress such activity over a longer term, comprising administering to them substantially daily an effective amount of a pharmacuetical composition comprising a phenylalkylhydrazine, for a minimum period of about several weeks to about a half dozen weeks.

2. Method of treating drug abusers according to claim 1, for a maximum period of about a half dozen to about a dozen months.

3. A method of treating patients for abusing drugs likely to enhance neurotransmitter activity in the short term and to depress such activity over a longer term, comprising administering to such a patient substantially daily an amount of phenelzine or equivalent phenylalkylhydrazine so as to effect monoamine oxidase inhibition incompatible with consumption of such an abused drug by rendering the abuser's reaction to consumption of the abused drug during the period of treatment very unpleasurable.

4. Treatment method according to claim 3, including selecting a daily dosage of such phenylalkylhydrazine such that a patient to whom it is administered exhibits a reduction of blood pressure from a sitting to a standing position and a further reduction of blood pressure from standing to jogging in place, while such pressure remains adequate throughout.

5. Method according to claim 3, wherein such monoamine oxidase inhibitory effect persists for about two weeks after conclusion of such treatment.

* * * * *